United States Patent
Goulu et al.

(10) Patent No.: US 10,492,491 B2
(45) Date of Patent: Dec. 3, 2019

(54) INSECTICIDE COMPOSITION INCLUDING A SYNERGISTIC AGENT

(71) Applicant: UNIVERSITE D'ANGERS, Angers (FR)

(72) Inventors: Mathilde Goulu, Fontaine-Milon (FR); Veronique Apaire-Marchais, Angers (FR); Olivier List, Bouchemaine (FR); Valerie Raymond, Bouchemaine (FR); Bruno Lapied, Angers (FR)

(73) Assignee: UNIVERSITE D'ANGERS, Angers (FR)

( * ) Notice: Subject to any disclaimer, the term of this patent is extended or adjusted under 35 U.S.C. 154(b) by 0 days.

(21) Appl. No.: 14/959,182

(22) Filed: Dec. 4, 2015

(65) Prior Publication Data

US 2017/0156331 A1   Jun. 8, 2017

(51) Int. Cl.
*A01N 37/18* (2006.01)
*A01N 37/46* (2006.01)

(52) U.S. Cl.
CPC ............ *A01N 37/18* (2013.01); *A01N 37/46* (2013.01)

(58) Field of Classification Search
CPC ........ A01N 25/08; A01N 37/18; A01N 37/44; A01N 43/88; A01N 47/40; A01N 37/46
See application file for complete search history.

(56) References Cited

U.S. PATENT DOCUMENTS

| | | | |
|---|---|---|---|
| 7,745,375 B2 * | 6/2010 | Andersch | A01N 51/00 504/134 |
| 2006/0211655 A1 | 9/2006 | Mencke | |
| 2006/0252728 A1 * | 11/2006 | Sirinyan | A01N 53/00 514/65 |
| 2007/0122437 A1 * | 5/2007 | Hougard | A01N 37/18 424/405 |
| 2009/0003640 A1 | 1/2009 | Burnett | |

FOREIGN PATENT DOCUMENTS

AU    2013237746    5/2015

OTHER PUBLICATIONS

Faulde et al. (Parasite Res (2012) 111:755-765).*
Search Report dated Jan. 13, 2016.
Search Report dated Jan. 25, 2017.
Frederic Darriet et al: "Efficacy of six neonicotinoid in secticides alone and in combination with deltamethrin and piperonyl butoxide against pyrethroid-resistant Aedes aegypti and Anopheles gambiae (Diptera: Culicidae)" Pest Management Science, vol. 69, No. 8, Dec. 4, 2012.
Office Action dated Nov. 1, 2018.
Lapied at el.: "Ionic Species Involved in the Electrical Activity of Single Adult Aminergic Neurones Isolated From the Sixth Abdominal Ganglion of the Cockroach Periplaneta Americana" Dated: 1989.
Mathilde Goulu.: Abstract of Oral presentation: "Quatriemes journees scientifiques de l'ecole doctorale venam" Dated: Dec. 4, 2014.
Bonnet et al.: "Parasites & Vectors" Dated: 2009.

* cited by examiner

*Primary Examiner* — Snigdha Maewall
(74) *Attorney, Agent, or Firm* — Ipsilon USA, LLP

(57) ABSTRACT

Insecticide composition where the active ingredient includes a combination of at least one synthetic insecticidal molecule from the neonicotinoïd family, and at least one synergistic agent, which is chosen among the insect repellent agents and present in the composition at a molar ratio of the synergistic agent to the synthetic insecticidal molecule in the composition comprised between 0.001 and 0.2. The insecticide includes a synergistic combination of DEET or IR3535® with thiacloprid or thiamethoxam that are more effective at low doses.

10 Claims, 3 Drawing Sheets

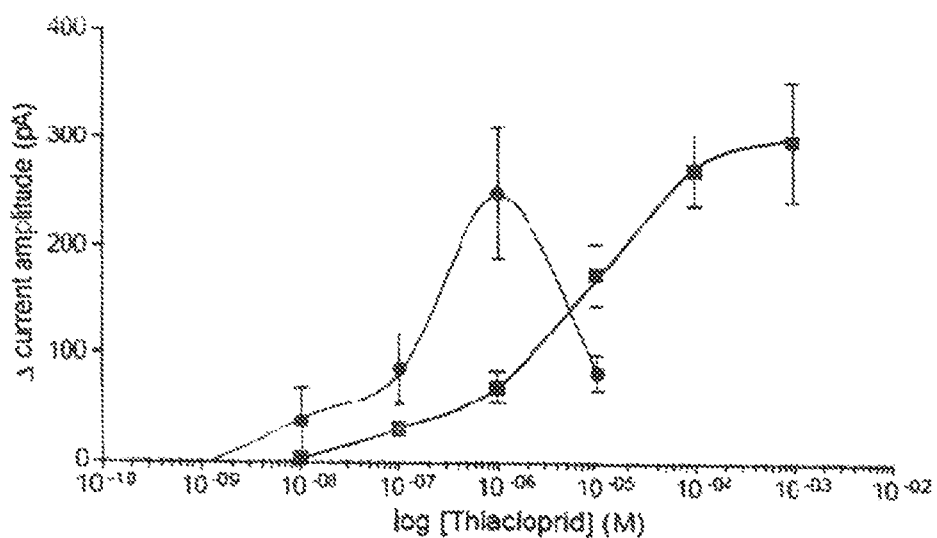
Fig. 5
Fig. 6A
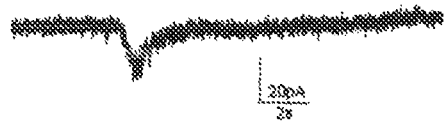
Fig. 6B
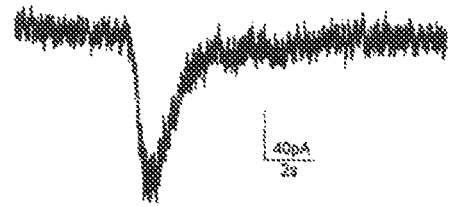
Fig. 6C
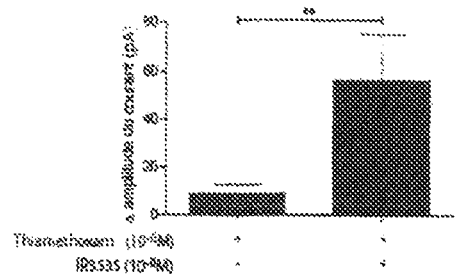

INSECTICIDE COMPOSITION INCLUDING A SYNERGISTIC AGENT

FIELD OF THE INVENTION

The present invention relates to new insecticide compositions, including a synergistic agent, in particular against mosquitoes, and more particularly in the field of the vector control, against mosquito-borne diseases.

BACKGROUND OF THE INVENTION

Climatic and social changes influence the distribution and the dynamics of mosquito-borne diseases thus contributing to the risk of emergence and resurgence of epidemics (malaria, dengue, chikungunya). For most mosquito-borne diseases, there is to date no vaccine and no curative treatment. The vector control and the prevention of mosquito bites are particularly based on the safe and efficacious use of chemicals. Because mosquitoes become resistant, it is essential to develop new strategies against insects to increase treatment efficacy and to circumvent resistance mechanisms.

Chemicals which have been classically used up to now are classified into two main categories, according to their mode of action: in the first category are insect repellent molecules which prevent mosquitoes of approaching their target and in the second category are insecticide molecules which "kill" the mosquitoes.

In the repellent molecules category, the broadly used insect repellent in the world is DEET (N,N-diethyl-3-methylbenzamide, previously named N,N-diethyl-m-toluamide). Other known insect repellents are Icaridin (KBR) and IR3535® (3-[N-Butyl-N-acetyl]-aminopropionic acid, ethyl ester). To be effective against most mosquitoes implies that they have to be usually employed at relatively high concentrations in the compositions to be applied for instance on clothes or nets. However a compromise should be found between efficacy and adverse effects.

Insecticide synthetic molecules which are widespread used against mosquitoes, are chosen in the pyrethroid, carbamate or organophosphate families. However mosquitoes have become more and more resistant to these chemicals, in particular to the pyrethroid insecticides which have been widely used for house spraying and impregnation of mosquito nets for instance for malaria control. New insecticide candidates are thus searched for.

Recent studies (Bonnet J. et al. (2009) *Multi-function oxidases are responsible for the synergistic interactions occurring between repellents and insecticides in mosquitoes*. Parasites & Vectors 2:17) have described the efficiency of the combination of a non-pyrethroid insecticide (propoxur from the carbamate family) with a repellent (DEET) against the main dengue vector mosquito *Aedes aegypti*.

A first aim of the invention is to provide a new composition which can be used in the control of pyrethroid resistant mosquitoes.

Another aim of the invention is to provide a composition which can help controlling the mosquito-borne diseases such as malaria, dengue and chikungunya.

Another aim of the invention is to provide an insecticide composition having an optimized insecticide treatment efficacy while reducing doses.

SUMMARY OF THE INVENTION

Within the inventors' search works to understand the mechanism of action of these molecules against mosquitoes, in particular against dengue, malaria and chikungunya mosquito vectors, it has now been found, surprisingly, that a combination of a molecule from the neonicotinoïd family (usually used for pests control in crops and inefficient alone against mosquitoes) and an insect repellent at very low concentration (i.e. under its sub-repellent level) may be active as insecticide composition against mosquitoes.

Consequently the present invention relates to an insecticide composition wherein the active ingredient comprises the combination of:
- at least one synthetic insecticidal molecule from the neonicotinoïd family, and
- at least one synergistic agent, which is chosen among the insect repellents and present in said composition at a molar ratio of said synergist agent to the synthetic insectidal molecule comprised between 0.001 and 0.2.

DETAILED DESCRIPTION OF THE INVENTION

More particularly, in the composition of the invention, the molar ratio of said synergistic agent to the synthetic insecticidal molecule is preferably comprised between 0.005 and 0.1, and more preferably comprised between 0.01 and 0.1.

For instance, the at least one synthetic insecticidal molecule from the neonicotinoïd family is present at a concentration between $10^{-7}$ M and $10^{-5}$ M in the composition.

Consequently, such a concentration will lessen toxicity for humans or non-target animals.

Preferably, the synthetic insecticidal molecule from the neonicotinoïd family is chosen among the group consisting of thiaclopride, thiamethoxam, and a mixture thereof. Such synthetic neonicotinoïd molecules have never been used alone against mosquitoes, and consequently never used for controlling the mosquito-borne diseases such as malaria, dengue and chikungunya.

Preferred concentrations in the composition are comprised between $3.10^{-7}$ M and $3.10^{-6}$ M for thiaclopride and comprised between $10^{-7}$ M and $3.10^{-6}$ M for thiamethoxam.

Said synergistic agent may be DEET, IR3535®, or a mixture thereof. Advantageously, DEET can be present at a concentration comprised between $3.10^{-8}$ M and $3.10^{-7}$ M in the composition. IR3535® may be present at still lower concentrations, comprised between $3.10^{-9}$ M and $3.10^{-8}$ M in the composition. At these concentrations both DEET and IR3535® are at a sub-repellent concentrations against insects, i.e. they have no repellent efficacy and no insecticide efficacy alone against insects, in particular against mosquitoes.

The insecticide composition of the present invention may be in a liquid form, the active ingredient being solubilized in an organic phase and/or encapsulated in nano- or microcapsules. It may be configured to be sprayed on, deposited on, or impregnated into a support or a material such as net, fabrics, cloth, tent, . . . to prevent insects to reach their targets.

This active combination in the composition of the invention can therefore be used against insects which are harmful to human, to animals and/or to crops, in particular against insects chosen from the group: diptera, dictyoptera, lepidoptera, orthoptera and hemiptera, thus providing ways of controlling insect vector-borne diseases.

The composition of the invention is particularly active against mosquitoes chosen from the group consisting of *Anophyles gambiae* (main vector of malaria) and *Aedes aegypti* (main vector of dengue fever, chikungunya and yellow fever viruses).

The resulting main advantage is a better protection with low dose, and therefore an expected reduction of side-effects for humans and non-target animals. Moreover the composition of the invention is efficient against mosquitoes which are resistant to pyrethroid insecticides. In addition, this strategy could also be used in the crop protection context.

FIGURES

The invention will be further described in the below embodiments given with reference to the accompanying drawings, in which.

FIG. 5 is the dose-response curve of the effect of thiacloprid-induced inward current applied alone (square symbols) and after pretreatment with IR3535® ($10^{-8}$ M) (round symbols); and FIGS. 6A-6C illustrate the effect of thiamethoxam-induced inward currents ($10^{-6}$ M), recorded under voltage-clamp condition, before (6A) and after pretreatment with IR3535® used at $10^{-8}$ M (6B), and FIG. 6C illustrates comparative histogram of the effect of IR3535® ($10^{-8}$ M) on the thiamethoxam-induced inward current amplitude.

EXAMPLES

Materials and Methods
Insect Neuronal Model

Experiments were carried out on cockroach Dorsal Unpaired Median (DUM) neurons. Cockroach neuronal preparations are commonly used as biomedical models for vertebrates and invertebrates and DUM neurons are, furthermore, electrophysiologically and pharmacologically well characterized since most of the biophysical and pharmacological properties of ionic currents and receptors underlying and modulating their spontaneous action potentials have been established by using the well-known patch-clamp technique.

Figure 1:
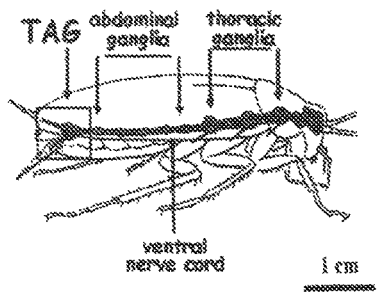
FIG. 1 illustrates the cockroach *Periplaneta americana* central nervous system used in the experiments.

Adult male cockroaches, *Periplaneta americana* (see FIG. 1), are taken from our laboratory colonies, which are maintained under standard conditions (29° C., photoperiod of 12 h light/12 h dark). Animals are immobilized dorsal-side up on a dissection dish. The dorsal cuticle, gut and some dorso-longitudinal muscles are removed to allow access to the ventral nerve cord. The abdominal nerve cord and its terminal abdominal ganglion (TAG), carefully dissected under a binocular microscope, are placed in normal saline. Animal care and handling procedures are in accordance with French institutional and national health guidelines.

The ventral nerve cord and its terminal abdominal ganglion (TAG) are carefully dissected under a binocular microscope and placed in normal cockroach saline containing (in mM) 200 NaCl, 3.1 KCl, 5 CaCl$_2$, 4 MgCl$_2$, 50 sucrose, and 10 N-2-hydroxymethylpiperazine-N9-2-ethanesulfonic acid (HEPES); pH was adjusted to 7.4 with NaOH. Isolation of adult DUM neuron cell bodies are performed under sterile conditions using enzymatic digestion and mechanical dissociation of the median parts of the TAG as previously described in Lapied et al. (*Ionic species involved in the electrical activity of single adult aminergic neurones isolated from sixth abdominal ganglion of cockroach Periplaneta americana* J Exp Biol 144:535-49, 1989). The isolated neuron cell bodies are used for recordings 24 h after dissociation.

Calcium Imaging

Falcon 1006 Petri dishes with glass coverslips are coated with poly-D-lysine hydrobromide (mol. wt. 70,000-150,000), and isolated DUM neuron cell bodies are plated. External recording solution contains (in mM): 200 NaCl; 3.1 KCl; 5 CaCl$_2$; 4 MgCl$_2$, and 10 HEPES buffer; pH is adjusted to 7.4 with NaOH. The cells are incubated in the dark with 10 µM Fura-2 pentakis (acetoxy-methyl) ester for 60 min at 37° C. After loading, cells are washed three times in saline. The glass coverslips are then mounted in a recording chamber (Warner Instruments, Hamden, Conn.) connected to a gravity perfusion system allowing drug application. Imaging experiments are performed with an inverted microscope (Nikon) equipped with epifluorescence. Excitation light is provided by a 75-W integral xenon lamp. Excitation wavelengths (340 nm and 380 nm) are applied using a computer driven a monochromate or (Sutter Instruments Company, Lambda DG4) with a digital charge-coupled device (CCD) camera (Hamamatsu Orca R$^2$) and they are recorded in the computer with calcium imaging software (Imaging Workbench 6, indec BioSystem). Exposure times at 340 nm and 380 nm are usually 150 ms, and images are collected at various frequencies. Data are expressed as the ratio of emitted fluorescence (340 nm/380 nm). Different concentrations of the insect repellent IR3535® ranging from $10^{-9}$ M to $10^{-5}$ M have been tested.

Electrophysiology and Whole-Cell Patch-Clamp Recordings

Electrical activity and neonicotinoïd-induced inward currents are recorded using the patch clamp technique in the whole-cell recording configuration under current-clamp and voltage-clamp mode, respectively. Patch-clamp electrodes are pulled from borosilicate glass capillary tubes (GC150T-10) using a P-97 model puller. Patch pipettes have resistances ranging from 1 to 1.2 MΩ when filled with internal pipette solution. The liquid junction potential between extracellular and intracellular solutions is always corrected before the formation of a giga Ohm seal (>3 GΩ). Signals are recorded with an Axopatch 200A amplifier. Ionic currents induced by thiamethoxam and/or by thiacloprid are displayed on a computer with software control pClamp connected to a digidata acquisition system (digidata 1320A). Under voltage-clamp conditions, DUM neuron somata are voltage-clamped at a steady state holding potential of −50 mV to measure the effects of thiamethoxam or thiacloprid applied alone and after pretreatment with IR3535® ($10^{-8}$ M). Experiments are carried out at room temperature.

Example 1

1.1—Dose-Dependent Effect of the Insect Repellent IR3535® on Insect Neurons

Using calcium imaging, it has been possible to study the effect of the insect repellent IR3535®, on the intracellular calcium concentration in insect DUM neurons. Bath application of IR3535® induces a complex multiphasic dose-dependent effect on the intracellular calcium concentration (see FIG. 2).

Figure 2A:
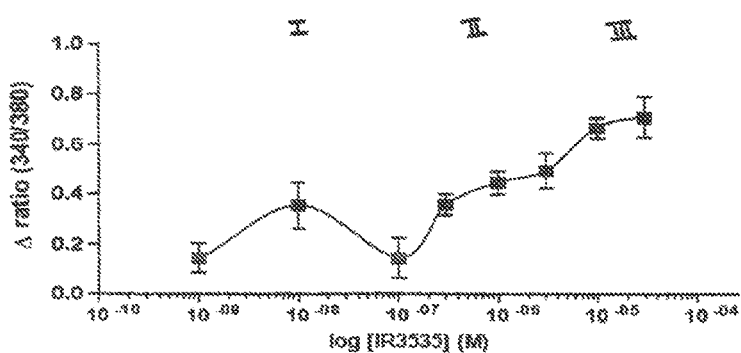
FIGS. 2A through 2D are curves showing the complex dose-dependent effects of IR3535® on DUM neuron intracellular calcium concentration.
Figures 2B, 2C, 2D:
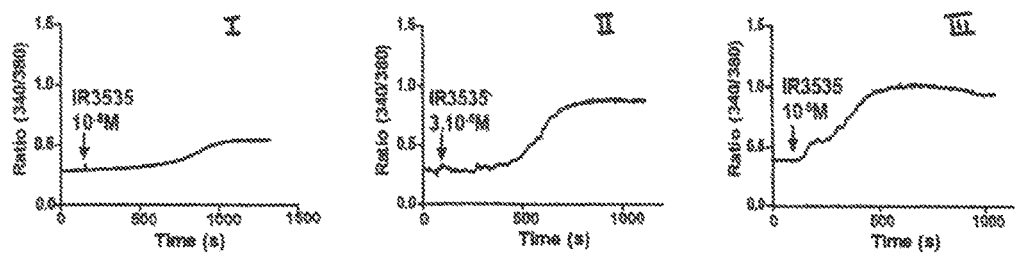

FIG. 2A shows the dose-response curve illustrating changes in intracellular calcium concentration depending on the different concentrations of IR3535® tested. Intracellular calcium concentration variations (presented as ratios 340/380) have been calculated from mean values obtained for each IR3535® concentration tested (n=5). FIGS. 2B to D represent spectrum of the intracellular calcium concentration rises induced by IR3535® tested at $10^{-8}$ M, $3.10^{-6}$ M and $10^{-5}$ M, respectively.

In zone I (FIGS. 2A and 2B), it is possible to observe a transient increase of intracellular calcium concentration between $3.10^{-9}$ M and $3.10^{-8}$ M, reaching a maximum for IR3535® used at $10^{-8}$ M, i.e. at a very low concentration.

Zone II corresponds to an additional elevation of intracellular calcium concentration obtained for IR3535® used in the concentration range from $10^{-7}$ M to $3.10^{-6}$ M (FIGS. 2A and 2C). Finally, zone III corresponds to the maximum effect produced by IR3535® used at very high concentration ($3.10^{-5}$ M) (FIGS. 2A and 2D). These results demonstrate that the insect repellent IR3535® exerts its effect through an elevation of intracellular calcium concentration in insect neurons.

1.2—Origin of the Intracellular Calcium Rise

Figure 3A:
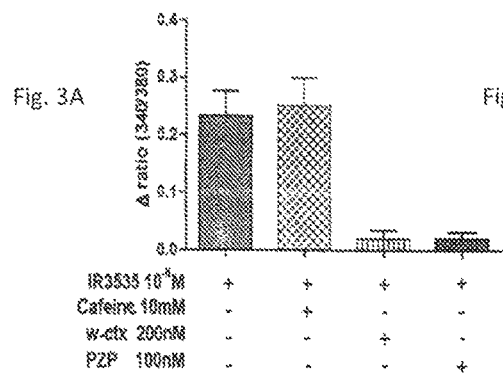
FIG. 3A and FIG. 3B are comparative histograms illustrating the effects of IR3535® used at $10^{-8}$ M (A) and $10^{-5}$ M (B) on the intracellular calcium concentration in the presence of different pharmacological agents.
Figure 3B:
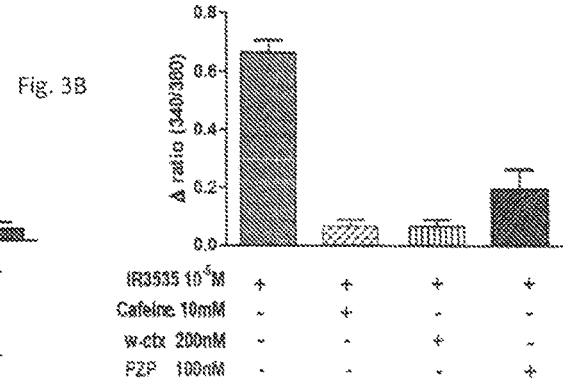

To determine the origin of the intracellular calcium concentration rise (i.e., intracellular and/or extracellular origin), different specific blockers and/or antagonists of calcium channels and membrane receptors have been tested. Histograms of FIG. 3 show the comparative effects of IR3535® used at $10^{-8}$ M (FIG. 3A) and $10^{-5}$ M (FIG. 3B) on the intracellular calcium concentration in the presence of different pharmacological agents such as caffeine, omegaconotoxin (ω-ctx) and pirenzepine (PZP).

From these results, inventors have determined that the effect of IR3535® used at $10^{-8}$ M results from extracellular calcium through plasma membrane voltage-dependent calcium channels via M1/M3 mAChR sub-type modulation. For higher concentrations of IR3535®, both extracellular calcium and calcium released from internal stores are involved in the effects of the repellent in insect neurons.

Figure 4A:
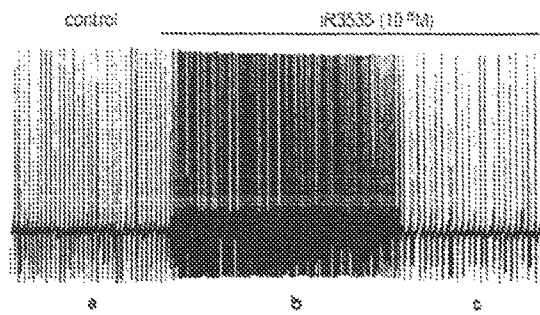
FIGS. 4A and 4B illustrate the effect of IR3535® used at $10^{-8}$ M on the DUM neuron spontaneous electrical activity (4A) and shows comparative histogram of the effects of IR3535® used at $10^{-8}$ M on action potential discharge frequency (4B)
Figure 4B:
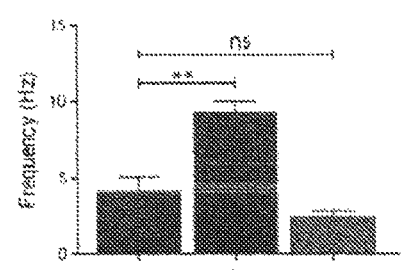

1.3—Effect of the Insect Repellent IR3535® on DUM Neuron Spontaneous Action Potentials From the data presented just above, it appears that $10^{-8}$ M is the lower concentration of IR3535®, which produces a significant elevation of intracellular calcium concentration in DUM neurons. Consequently, the following experiments have been performed using $10^{-8}$ M IR3535®. Using the patch clamp technique in the whole-cell recording configuration, it has been possible to show that IR3535® ($10^{-8}$ M) induces a significant membrane depolarization associated with an increase of the spontaneous action potential discharge frequency (FIG. 4A). The corresponding FIG. 4B illustrates comparative histogram of the effect of IR3535® ($10^{-8}$ M) on the spontaneous action potential discharge frequency.

According to the results presented above, using different pharmacological agents, calcium imaging and electrophysiological technique, and based on previous results obtained on the same neuronal preparation, it is possible to summarize the effect of IR3535® used at very low concentration on the intracellular calcium concentration in DUM neurons. IR3535®, by acting on M1/M3 mAChR sub-types, inhibits background calcium-activated potassium channels resulting in the small depolarization observed. This membrane depolarization is sufficient to stimulate N-type high-voltage activated calcium channels involved in the calcium influx through the membrane.

Example 2—Dose-Dependent Effect of the Insect Repellent DEET on Insect Neurons

Similar experiments as example 1 have been made with DEET at different concentrations.

Application of the insect repellent DEET onto insect neurons produces a biphasic effect on intracellular calcium concentration changes. In the low concentration range (from $10^{-9}$ M to $10^{-7}$ M), DEET induces an elevation of the intracellular calcium concentration reaching a maximum at $10^{-7}$ M (ratio of emitted fluorescence (340 nm/380 nm) ranging from 0.4 to 0.6 with a maximum value obtained at 0.7).

For higher concentrations than $10^{-7}$ M, DEET produces an opposite effect (i.e. an important decrease of the intracellular calcium concentration.

Therefore, preferred referend concentrations of DEET as synergist agent should therefore be chosen between $3.10^{-8}$ M and $3.10^{-7}$ M where the ratio of emitted fluorescence (340 nm/380 nm) is above 0.6.

Example 3—Synergistic Effect Occurring Between IR3535®/Thiacloprid or IR3535®/Thiamethoxam Neonicotinoïd insecticides thiacloprid and thiamethoxam have been tested alone and after pretreatment with IR3535® ($10^{-8}$ M) on DUM neurons using the patch-clamp technique, under voltage clamp condition (FIG. 5 and FIG. 6).

3.1—Effects of Thiacloprid Alone and after Pretreatment of DUM Neuron by IR3535®

Bath application of thiacloprid alone produces a dose-dependent increase of the inward current amplitude (FIG. 5, square symbols) with a maximum effect reached at $10^{-3}$ M. When DUM neuron is pretreated with the repellent IR3535® used at $10^{-8}$ M (ranging from $10^{-8}$ M to $10^{-6}$ M) (round symbols) an increase of the inward current amplitude is maximum at $10^{-6}$ M thiacloprid. For higher concentration of thiacloprid ($10^{-5}$ M), opposite effect is observed resulting in an important decrease of the current amplitude.

3.2 Effects of Thiamethoxam Alone and after Pretreatment of DUM Neuron by IR3535®

Application of thiamethoxam ($10^{-6}$ M) alone induces an inward current with small amplitudes (see FIG. 6A: recorded under voltage-clamp condition, at holding potential of −50 mV, and FIG. 6C) (means+S.E.M., **, p<0.01 (n=3-4)).

By contrast, after pretreatment of DUM neuron with the repellent IR3535® used at $10^{-8}$ M an important increase of the thiamethoxam-induced inward current amplitude is observed. In this case, the mean current amplitude is surprisingly about 6-fold more important than the current amplitude obtained with thiamethoxam applied alone (FIGS. 6B and 6C).

In conclusion, complementary approaches such as calcium imaging and electrophysiology reveal that the neonicotinoïd insecticides thiacloprid or thiamethoxam act like agonists able to induce an inward current with a small amplitude. When DUM neurons are pretreated with low concentration of IR3535®, the inward current amplitude produces by thiamethoxam or by thiacloprid is more important. This confirms the role of IR3535® as synergistic agent, which can increase the effect of the neonicotinoïd insecticides thiacloprid or/and thiamethoxam via an increase of intracellular calcium concentration. These results confirm that combining the repellent IR3535® with a neonicotinoïd insecticide could be an interesting alternative to 1) circumvent resistance mechanisms developed by mosquitoes-borne diseases and 2) increase insecticide efficacy while reducing doses.

The invention claimed is:

1. Insecticide composition for pyrethroid resistant mosquitoes wherein the active ingredient is the combination, without any pyrethroid insecticide, of:

a synthetic insecticidal molecule from the neonicotinoïd family at a concentration between $10^{-7}$ M and $10^{-5}$M in the composition, wherein the synthetic insecticidal molecule from the neonicotinoïd family is thiaclopride, and at least one synergistic agent, which is chosen among the insect repellents and present in said composition under its sub-repellent level, and at a molar ratio of said synergistic agent to the synthetic insecticidal molecule of the neonictinoid family in the composition comprised between 0.001 and 0.2.

2. Composition according to claim 1, wherein the molar ratio of said synergistic agent to the synthetic insecticidal molecule in the composition is comprised between 0.01 and 0.1.

3. Composition according to claim 1, wherein thiaclopride is present at a concentration comprised between $3 \cdot 10^{-7}$ M and $3 \cdot 10^{-6}$ M in the composition.

4. Composition according to claim 1, wherein said synergistic agent is 3-[N-butyl-N-acetyl]-amino propionic acid, ethyl ester.

5. Composition according to claim 1, wherein said composition is in a liquid form, the active ingredient being either one of solubilized in an organic phase and/or encapsulated in nano or micro-capsules.

6. Composition according to claim 1, wherein said composition is configured to be deposited on, or impregnated into a net, fabrics, cloth or tent.

7. Composition according to claim 1, wherein said combination is active against insects which are harmful to human, to animals and/or to crops.

8. Composition according to claim 7, wherein said combination is active against insects which are harmful to insects chosen from the group consisting of diptera, dictyoptera, lepidoptera, orthoptera and hemiptera.

9. Composition according to claim 8, wherein said composition is active against mosquitoes chosen among the group consisting of *Anophyles gambiae* and *Aedes aegypti*.

10. Composition according to claim 4, wherein said synergistic agnet is present at a concentration comprised between $3 \cdot 10^{-9}$M and $3 \cdot 10^{-8}$M in the composition.

* * * * *